United States Patent [19]

Damani

[11] Patent Number: 4,892,890
[45] Date of Patent: Jan. 9, 1990

[54] EXTERNAL ANALGESIC COMPOSITIONS

[75] Inventor: Nalinkant C. Damani, Cincinnati, Ohio

[73] Assignee: G. D. Searle and Company, Chicago, Ill.

[21] Appl. No.: 859,594

[22] Filed: May 5, 1986

Related U.S. Application Data

[63] Continuation-in-part of Ser. No. 667,036, Nov. 1, 1984, abandoned.

[51] Int. Cl.⁴ ............................ A61K 9/00; A61K 9/06
[52] U.S. Cl. ..................................... 514/784; 514/785; 514/786; 514/953; 514/969; 424/DIG. 5; 424/59; 424/60; 424/64
[58] Field of Search ......................... 424/59, 60, 63, 64, 424/DIG. 5, 15; 514/784, 785, 786, 969, 953

[56] References Cited

U.S. PATENT DOCUMENTS

| | | | |
|---|---|---|---|
| 2,538,127 | 1/1951 | Saunders et al. | 424/DIG. 15 |
| 2,696,456 | 12/1954 | Hetterick | 424/DIG. 15 |
| 2,975,099 | 3/1961 | Goyan et al. | 424/DIG. 15 |
| 3,122,475 | 2/1964 | Schalppi | 424/DIG. 15 |
| 3,644,613 | 2/1972 | Moeller et al. | 424/49 |
| 3,914,131 | 10/1975 | Hutchinson | 424/64 |
| 4,136,163 | 1/1979 | Watson et al. | 424/48 |
| 4,151,272 | 4/1979 | Geary et al. | 424/66 |
| 4,229,432 | 10/1980 | Geria | 424/68 |
| 4,280,994 | 7/1981 | Turney | 424/68 |
| 4,347,237 | 8/1982 | Evenstad et al. | 424/DIG. 15 |
| 4,368,185 | 1/1983 | Mizuno et al. | 424/DIG. 15 |
| 4,425,328 | 1/1984 | Nabial | 424/66 |
| 4,504,465 | 3/1985 | Sampson et al. | 424/DIG. 5 |
| 4,678,663 | 7/1987 | Scott et al. | 424/60 |
| 4,695,452 | 9/1987 | Gannis et al. | 424/60 |
| 4,702,916 | 10/1987 | Geria | 424/DIG. 5 |
| 4,722,836 | 2/1988 | Geary et al. | 424/DIG. 5 |
| 4,725,432 | 2/1988 | May | 424/DIG. 5 |

FOREIGN PATENT DOCUMENTS

| | | | |
|---|---|---|---|
| 1018M | 3/1961 | France | 424/DIG. 15 |
| 1031M | 3/1961 | France | 424/DIG. 15 |
| 1760M | 1/1962 | France | 424/DIG. 15 |
| 1986M | 7/1962 | France | 424/DIG. 15 |
| 4340M | 3/1965 | France | 424/DIG. 15 |
| 5653611 | 5/1908 | Japan . | |

OTHER PUBLICATIONS

P. Skierkowski & N. C. Lublanezki, "External Analgesic Products", in *Handbook of Nonprescription Drugs*, 7th ed.; APA and National Prof. Soc. Pharmacists: Washington, D.C., 1982; pp. 513–523.

H. E. Jass, "The History of Antiperspirant Product Development", *Cosmetics and Toiletries*, 95, 25–31 (1980).

G. S. Kass, "Deodorant and Antiperspirant Formulary", *Cosmetics and Toiletries*, 95, 57–72 (1980).

P.D.R. 6th ed. (1985) for Nonprescription Drugs, pp. 424, "Chapstick Lip Balm Lip Soother", p. 428, Icy Hot Analgesic Balm and Rub, pp. 512, 519, 550, 567, 595, 596, 604, 605, 638, 654, 655, 656, 682, 705, Deep–Down Rub, Work-Out Rub, Banalg, Analgesic Balm, Ben-–Gay, Rectal Medicone Suppositories, Mentholatum Lotion, Rub, Lip Balm, Ointment, Chapstick Lip Balm, Lip Soother, Icy Hot Balm, Rub, Vicks Vaporub Ointments.

*Primary Examiner*—Shep K. Rose
*Attorney, Agent, or Firm*—Paul Matukaitis; R. E. L.f Henderson; Joy A. Serauskas

[57] ABSTRACT

The present disclosure relates to an external analgesic solid stick composition for the topical administration of active analgesic agents. The compositions are dimensionally stable solid compositions comprising an external analgesic agent incorporated into a non-reactive hydrophobic wax matrix.

5 Claims, No Drawings

EXTERNAL ANALGESIC COMPOSITIONS

This application is a continuation-in-part of application Ser. No. 06/667,036 filed Nov. 1, 1984, now abandoned.

BACKGROUND OF THE INVENTION

The present invention relates to a solid stick external analgesic composition. More particularly, this invention relates to physically and chemically stable solid stick compositions for the topical administration of salicylate esters.

Externally applied analgesic compositions are useful in providing relief from minor pain and discomfort in muscles and joints. Such external analgesics may exhibit topical analgesic, topical anesthetic, topical antipruritic, or counterirritant effects. See P. Skierkowski and N. C. Lublanezki, "External Analgesic Products," in *Handbook of Nonprescription Drugs*, 7th ed.; American Pharmaceutical Association and the National Professional Society of Pharmacists: Washington, D.C., 1982; pp. 513–523. Because counterirritants abate the perception of pain and induce a mild inflammatory reaction, thereby producing a feeling of warmth, counterirritant drugs are commonly used external analgesics. Since methyl salicylate, also known as oil of wintergreen, is considered safe and effective and has a pleasant aroma, it is the most widely used topical counterirritant. External analgesic products are commercially available in various fluid forms, such as lotions, ointments, creams, gels, sprays, and the like, and are typically formulated with other active components, such as menthol, methyl nicotinate, camphor, and the like. See, e.g., Skierkowski and Lublanezki, pp. 521–523. Since these fluid forms are typically applied with an applicator or with the fingers, a chemically and physically stable solid stick form would be neater and more convenient.

Solid sticks are well-established delivery forms for topically applied drugs and cosmetics, being particularly useful for lipsticks, deodorants, and antiperspirants. In general, a solid stick consists of an essentially solid matrix that serves as the base for some active ingredient or cosmetic substance. Typical deodorant sticks, which contain ingredients to mask odors or eliminate their cause but which do not contain an antiperspirant agent, are in effect ethanol gelled With sodium stearate. Since antiperspirant sticks incorporate an astringent, generally aluminum chlorohydrate, that tends to be inactivated under alkaline conditions, the ethanol-stearate formulations used in deodorant sticks are generally unsatisfactory for antiperspirant sticks. Using other lower alcohols or other metal stearate salts will not significantly reduce the problem. Modern antiperspirant stick formulations avoid the alkalinity that inactivates the astringent by employing a hydrophobic waxy matrix. To improve sensory perception and facilitate smooth application, various additives, particularly volatile silicones such as cyclomethicone (silicone VS-7158), are also included in the formulations. See (1) H. E. Jass, "The History of Antiperspirant Product Development," *Cosmetics and Toiletries*, 95, 25–31 (1980); and (2) G. S. Kass, "Deodorant and Antiperspirant Formulary," *Cosmetics and Toiletries*, 95, 57–72 (1980). See also U.S. Pat. Nos. 4,425,328, 4,280,994, and 4,229,432 for examples of antiperspirant stick compositions.

External analgesics, including methyl salicylate, have been formulated in solid stick form using a stearate-alcohol-water matrix. See, e.g., Japan Kokai Patent No. 56-53611. To eliminate possible alkaline degradation of methyl salicylate and concomitant release of methanol by transesterification (due to ethanol) or by hydrolysis (due to moisture), it would be more desirable to formulate the stick using a less reactive matrix. Therefore to avoid such alkaline degradation of salicylate esters it is an object of the present invention to provide an external analgesic solid stick composition containing salicylate esters incorporated into a non-reactive hydrophobic waxy matrix.

SUMMARY OF THE INVENTION

The present invention relates to a chemically and physically stable external analgesic solid stick composition formulated by incorporating pharmaceutically effective amounts of one or more external analgesic agents into a non-reactive hydrophobic waxy matrix. In particular the compositions of the present invention are effective when one of the external analgesic agent is a lower aklyl salicylate ester. The waxy matrix comprises one or more fatty substances such as triglycerides, long-chain fatty acids or long-chain fatty alcohols combined with one or more waxy substances such as paraffins, esters of long-chain fatty acids or esters of long-chain fatty alcohols. In addition, in order to provide the requisite sensory properties important to consumer perception, the non-reactive hydrophobic waxy matrix may optionally contain plasticizers, non-hydroxylic volatile silicone compounds and penetration enhancers. The non-reactive hydrophobic waxy matrix prevent the degradation of salicylate esters when such salicylate esters are employed as the external analgesic agent.

The external analgesic compositions of the present invention provide for the topical administration of external analgesic agents and are useful for the relief of minor pain and discomfort in muscles and joints. In addition to being chemically stable, the external analgesic solid stick compositions of the present invention are dimensionally stable solid compositions that do not deform despite normal climatic temperature variations, deposit smoothly on the skin without leaving heavy solid residues, and provide the preception of warmth associated with external analgesic agents.

DETAILED DESCRIPTION OF THE INVENTION

The present invention relates to an external analgesic solid stick composition comprising pharmaceutically effective amounts of one or more external analgesic agent incorporated into a non-reactive hydrophobic waxy medium. The external analgesic agents employed in the compositions of the present invention are readily ascertained by one of ordinary skill in the art and include, for example, lower alkyl salicylate esters, such as methyl salicylate and ethyl salicylate; menthol; methyl nicotinate; histamine hydrochloride; camphor; eucalyptol; capsaicin and the like. The preferred external analgesic agents include lower alkyl salicylate esters, menthol, histamine hydrochloride, and camphor. The most preferred external analgesic agents are lower alkyl salicylate esters, in particular methyl salicylate. In addition, although the external analgesic agents may be employed individually in the compositions of the present invention, it is preferred to employ two or more external analgesic agents, such as a mixture of methyl salicylate and menthol.

In order to prevent the degradation of the active external analgesic agent, in particular any lower alkyl salicylate ester, it is necessary to incorporate the external analgesic agent into a non-reactive hydrophobic waxy matrix. The term "non-reactive hydrophobic waxy matrix" refers to mixtures of fats and waxes and any other components excluding water and any alcohols, such as methanol, ethanol and the like that react with any of the external analgesic agents, in particular the salicylate esters. The non-reactive hydrophobic waxy matrix employed in the compositions of the present invention are readily ascertained by one of ordinary skill in the act and include mixtures of various fats and wax substances. The mixture of fats and wax substances employed herein provide the physical support for the solid matrix and are dimensionally stable, that is, are resistant to flow or deformation. In particular, the non-reactive hydrophobic waxy matrix remains essentially rigid despite normal temperature variations.

As used herein, the term "fats" or "fatty substances" includes triglycerides, long-chain fatty acids having from 10 to 30 carbon atoms, and long-chain fatty alcohols having from 10 to 30 carbon atoms. The term "triglycerides" as used herein refers to triesters of long-chain fatty acids having from 10 to 30 carbon atoms. Illustrative of the long-chain fatty acids employed in the compositions of the present invention include, for example, lauric acid, myristic acid, stearic acid, palmitic acid and the like. Illustrative of the long-chain fatty alcohols employed herein include lauryl alcohol, myristyl alcohol, stearyl alcohol, cetyl alcohol and the like. It is preferred to employ mixtures of the long-chain fatty acids and long-chain fatty alcohols. It is most preferred to employ mixtures of stearic acid and stearyl alcohol.

As used herein, the term "wax substances" includes paraffins, esters of long-chain fatty acids having from 10 to 30 carbon atoms, and esters of long-chain fatty alcohols having from 10 to 30 carbon atoms. The term "paraffins" includes mixtures of hydrocarbons having from 20 to 32 carbon atoms. It is preferred to employ mixtures of the paraffins, esters of long chain fatty acids and esters of long-chain fatty alcohols.

As previously noted, in addition to the fats and wax substances, the non-reactive hydrophobic wax matrix of the present invention may include other components such as various plasticizers, non-hydroxylic volatile substances and/or penetration enhancers. Such components provide the sensory properties important to consumer perception, and may improve delivery and absorbtivity of the external analgesic agent on the skin.

The term "plasticizers" includes substances that enhance flexibility and mobility by controlling crystal growth within the solid matrix. In particular, plasticizers inhibit any tendency of fats and wax substances to form crystalline inclusions. Examples of plasticizers useful in the compositions of the present invention include polyethylene glycols (PEG's), propylene glycol, and other polyhydric alcohols, as well as ester derivatives thereof. The preferred plasticizers are polyethylene glycol distearates.

To enhance the application or delivery of the external analgesic agent, it is preferred to employ a volatile substance which will essentially evaporate when applied to the skin. However, as previously noted, in order to reduce undesirable chemical decomposition of the external analgesic agents, in particular methyl salicylate, it is necessary to exclude water and reactive lower alcohols such as methanol, ethanol and the like from the compositions of the present invention. Therefore, it is necessary to employ non-hydroxylic volatile compounds, in particular volatile silicones such as cyclic siloxanes. The non-hydroxylic volatile silicones not only reduce the tackiness with the fats and wax substances employed in the wax matrix, but also have an inherent smoothness when applied to the skin. Representative of the cyclic siloxanes that may be utilized include octamethylcyclotetrasiloxane, decamethylcyclopentasiloxane, dodecamethylcyclohexasiloxane, and mixtures thereof (such as cyclomethicone, in which the cyclic pentamer predominates).

The "penetration enhancers" employed in the present invention include substances that improve transdermal penetration and absorption of active ingredients. An example of a preferred penetration enhancer is propylene glycol, which may also be utilized as a plasticizer in the compositions of the present invention.

The specific amounts of plasticizers, volatile silicones and penetration enhancers employed in the compositions of the present invention are readily ascertained by one of ordinary skill in the art.

In addition to the plasticizers, volatile silicones and penetration enhancers, other materials may be added to the non-reactive hydrophobic wax matrix for various specific purposes. Such other materials include but are not limited to other medicaments, perfumes, oils, coloring agents, pigments, fillers, stabilizing agents, germicides and the like.

A preferred embodiment of the present invention comprises an external analgesic solid stick composition comprising about 5 to 75% by weight of an external analgesic agent incorporated into a non-reactive hydrophobic waxy matrix comprising about 25 to 95% of said composition and consisting essentially of (a) about 5 to 40% by weight of a triglyceride, a long-chain fatty acid having from about ten to thirty carbon atoms, or a long-chain fatty alcohol having from about ten to thirty carbon atoms;

(b) about 10 to 60% by weight of a paraffin, esters of long-chain fatty acids having from 10 to 30 carbon atoms, or esters of long-chain fatty alcohols having from 10 to 30 carbon atoms;

(c) about 0 to 25% by weight of a plasticizer;

(d) about 0 to 40% by weight of non-hydroxylic volatile silicones; and (e) about 0 to 25% by weight of a penetration enhancer.

A more preferred embodiment of the present invention comprises compositions comprising about 10 to 30% by weight of methyl salicylate, either alone or in combination with about 3 to 16% by weight of one or more other external analgesics (preferably menthol), incorporated within a non-reactive hydrophobic waxy matrix comprising about 0 to 30% by weight of stearic acid and 0 to 30% by weight of stearyl alcohol, together being about 10 to 30% by weight; 10 to 40% by weight of paraffins; 1 to 25% by weight of polyethylene glycol (PEG) esters; 1 to 20% by weight of non-hydroxylic volatile silicones; and 3 to 25% by weight of propylene glycol.

The most preferred compositions of this invention comprise about 15% by weight of methyl salicylate and 8% by weight of menthol incorporated within a non-reactive hydrophobic wax matrix comprising 8% by weight of stearic acid, 9% by weight of stearyl alcohol, 9% by weight of Eskar wax R-25, 9% by weight of Eskar wax R-50, 6% by weight of microcrystalline wax W-835, 3% by weight of ceresin 101, 3% by weight of castorwax, 6% by weight of PEG-150 distearate, 10% by weight of cyclomethicone (e.g., silicone VS-7158), and 15% by weight of propylene glycol.

The preferred external analgesic solid stick compositions of the present invention may be prepared in accordance with the following procedure:

In general, the external analgesic agents are incorporated into the solid matrix by physically mixing liquified components. The methods used to prepare the compositions of this invention are selected for convenience in accordance with methods known to those skilled in the art. For example, higher melting components maybe heated together to form a melt, to which is then added a mixture of the lower melting or liquid components. Since methyl salicylate and the non-hydroxylic volatile silicones are liquids and menthol is a low-melting solid, these ingredients may conveniently be mixed with only moderate warming (e.g., about 30°–50° C. for the preferred compositions) to form a liquid. The remaining somewhat higher melting ingredients are mixed and then heated with stirring until melted (e.g., about 65°–85° C.). Although the order of mixing is not critical, it is generally more convenient to add the lower melting mixture to the hot melt. The resultant mixture is then allowed to cool somewhat (e.g., to about 55°–60° C. for the preferred compositions) for pouring into a mold where it is allowed to cool. The mold may be a form from which the stick is removed for inserting into a dispenser or it may be the ultimate dispenser itself.

The following examples further illustrate details of the composition of the present invention. The invention, which is set forth in the foregoing disclosure, is not to be construed or limited either in spirit or in scope by these examples. Those skilled in the art will readily understand that known variations of the conditions and processes of the following can be used for these compositions. All percentages are percent by weight unlike otherwise noted.

EXAMPLE 1

An external analgesic solid stick composition was prepared having the following composition:

| Ingredient | Percent (by weight) |
|---|---|
| Methyl salicylate | 15.0 |
| Menthol | 8.0 |
| Silicone VS-7158 | 10.0 |
| Propylene glycol | 15.0 |
| PEG-150 distearate | 5.0 |
| Stearyl alcohol | 9.0 |
| Stearic acid | 8.0 |
| Eskar wax R-25 | 9.0 |
| Eskar wax R-50 | 9.0 |
| Microcrystalline wax W-835 | 6.0 |
| Ceresin 101 | 3.0 |
| Castorwax | 3.0 |

The methyl salicylate, menthol, and non-hydroxylic volatile silicone (Silicone VS-7158) ingredients were mixed in the weight proportions indicated and then warmed until completely liquid (about 40° C.±10° C.). The remaining ingredients were mixed in the weight proportions indicated and then heated with stirring until melted (about 75° C.±10° C). The first liquid was added with mixing to the melt, and the resultant mixture was allowed to cool to about 62° C. (±5° C.). The mixture was poured into a product dispenser or into molds and then allowed to cool to room temperature.

EXAMPLE 2

An external analgesic solid stick composition was prepared having the following composition:

| Ingredient | Percent (by weight) |
|---|---|
| Methyl salicylate | 15.0 |
| Menthol | 8.0 |
| Silicone VS-7158 | 10.0 |
| Propylene glycol | 15.0 |
| PEG-150 distearate | 5.0 |
| Stearyl alcohol | 17.0 |
| Eskar wax R-25 | 9.0 |
| Eskar wax R-50 | 9.0 |
| Microcrystalline wax W-835 | 6.0 |
| Ceresin 101 | 3.0 |
| Castorwax | 3.0 |

The composition of this Example was prepared using the method described in Example 1.

EXAMPLE 3

An external analgesic solid stick composition was prepared having the following composition:

| Ingredient | Percent (by weight) |
|---|---|
| Methyl salicylate | 15.0 |
| Menthol | 8.0 |
| Silicone VS-7158 | 10.0 |
| Propylene glycol | 15.0 |
| PEG-150 distearate | 5.0 |
| Stearic acid | 17.0 |
| Eskar wax R-25 | 9.0 |
| Eskar wax R-50 | 9.0 |
| Microcrystalline wax W-835 | 6.0 |
| Ceresin 101 | 3.0 |
| Castorwax | 3.0 |

The composition of this Example was prepared using the method described in Example 1.

EXAMPLE 4

An external analgesic solid stick composition was prepared having the following composition:

| Ingredient | Percent (by weight) |
|---|---|
| Methyl salicylate | 30.0 |
| Menthol | 10.0 |
| Silicone VS-7158 | 10.0 |
| Propylene glycol | 3.0 |
| PEG-150 distearate | 5.0 |
| Stearyl alcohol | 3.0 |
| Stearic acid | 10.0 |
| Eskar wax R-50 | 18.0 |
| Microcrystalline wax W-835 | 5.0 |
| Ceresin 101 | 3.0 |
| Castorwax | 3.0 |

The composition of this Example was prepared using the method described in Example 1.

Although this invention has been described with respect to specific modifications, the details thereof are not to be construed as limitations, for it will be apparent that various equivalents, changes and modification may be resorted to without departing from the spirit and scope thereof, and it is understood that such equivalent embodiments are intended to be included therein.

What is claimed is:

1. An external analgesic solid stick composition comprising about 10 to 30% by weight of methyl salicylate and about 3 to 16% by weight of menthol incorporated within a non reactive hydrophobic wax matrix comprising
   (a) about 5 to 25% by weight of stearic acid, about 5 to 25% by weight of stearyl alcohol, together being about 10 to 30% by weight;
   (b) about 10 to 40% by weight of paraffins, esters of long-chain fatty acids having from 10 to 30 carbon atoms, or esters of long-chain fatty alcohols having from 10 to 30 carbon atoms;
   (c) about 1 to 25% by weight of polyethylene glycol (PEG) esters;
   (d) about 1 to 20% by weight of non-hydroxylic volatile silicones; and
   (e) about 3 to 25% by weight of propylene glycol
wherein said composition excludes water and reactive lower alcohols.

2. A composition according to claim 1 comprising about 15% by weight of methyl salicylate and about 8% by weight of menthol incorporated within a non-reactive hydrophobic wax matrix comprising
   (a) about 8% by weight of stearic acid, about 9% by weight of stearyl alcohol;
   (b) about 30% by weight of paraffins, esters of long-chain fatty acids having from 10 to 30 carbon atoms, or esters of long chain fatty alcohols having from 10 to 30 carbon atoms;
   (c) about 5% by weight of polyethylene glycol (PEG) esters;
   (d) about 10% by weight of non-hydroxylic volatile silicones; and
   (e) about 15% by weight of propylene glycol
wherein said composition excludes water and reactive lower alcohols.

3. A composition according to claim 1 comprising about 30% by weight of methyl salicylate and about 10% by weight of menthol incorporated within a non-reactive hydrophobic wax matrix comprising
   (a) about 10% by weight of stearic acid, about 3% by weight of stearyl alcohol;
   (b) about 29% by weight of paraffins, esters of long-chain fatty acids having from about 10 to 30 carbon atoms, or esters of long-chain fatty alcohols having from about 10 to 30 carbon atoms;
   (c) about 5% by weight of polyethylene glycol (PEG) esters;
   (d) about 10% by weight of non hydroxylic volatile silicones; and
   (e) about 3% by weight of propylene glycol
wherein said composition excludes water and reactive lower alcohols.

4. An external analgesic solid stick composition comprising 15% by weight of methyl salicylate and 8% by weight of menthol incorporated within a non-reactive hydrophobic wax matrix comprising
   (a) about 17% by weight of stearyl alcohol;
   (b) about 30% by weight of paraffins, esters of long-chain fatty acids having from about 10 to 30 carbon atoms, or esters of long-chain fatty alcohols having from about 10 to 30 carbon atoms;
   (c) about 5% by weight of polyethylene glycol (PEG) esters;
   (d) about 10% by weight of non-hydroxylic volatile silicones; and
   (e) about 15% by weight of propylene glycol
wherein said composition excludes water and reactive lower alcohols.

5. An external analgesic solid stick composition comprising 15% by weight of methyl salicylate and 8% by weight of menthol incorporated within a non-reactive hydrophobic waxy matrix comprising
   (a) about 17% by weight of stearic acid;
   (b) about 30% by weight of paraffins, esters of long-chain fatty acids having from 10 to 30 carbon atoms, or esters of long-chain fatty alcohols having from 10 to 30 carbon atoms;
   (c) about 5% by weight of polyethylene glycol (PEG) esters;
   (d) about 10% by weight of non- hydroxylic volatile silicones; and
   (e) about 15% by weight of propylene glycol
wherein said composition excludes water and reactive lower alcohols.

* * * * *